(12) United States Patent
Nozaki

(10) Patent No.: US 8,080,365 B2
(45) Date of Patent: Dec. 20, 2011

(54) THIOPYRAN DERIVATIVE, POLYMER, RESIST COMPOSITION, AND METHOD FOR MANUFACTURING SEMICONDUCTOR DEVICE USING SUCH RESIST COMPOSITION

(75) Inventor: Koji Nozaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 35 days.

(21) Appl. No.: 12/815,462

(22) Filed: Jun. 15, 2010

(65) Prior Publication Data
US 2010/0248154 A1 Sep. 30, 2010

Related U.S. Application Data

(60) Division of application No. 12/783,212, filed on May 19, 2010, which is a continuation of application No. PCT/JP2007/074128, filed on Dec. 14, 2007.

(51) Int. Cl.
G03F 7/30 (2006.01)
(52) U.S. Cl. .......................... 430/311; 430/326; 430/910
(58) Field of Classification Search .................. 430/311, 430/326, 910
See application file for complete search history.

(56) References Cited

U.S. PATENT DOCUMENTS

| | | | |
|---|---|---|---|
| 2003/0215736 A1* | 11/2003 | Oberlander et al. | 430/270.1 |
| 2005/0049325 A1 | 3/2005 | Chisholm et al. | |
| 2005/0049376 A1 | 3/2005 | Chisholm et al. | |
| 2005/0214674 A1* | 9/2005 | Sui et al. | 430/270.1 |
| 2008/0009647 A1 | 1/2008 | Hatakeyama et al. | |

FOREIGN PATENT DOCUMENTS

| | | |
|---|---|---|
| JP | 09-110790 A | 4/1997 |
| JP | 2005-133071 A | 5/2005 |
| JP | 2006-089412 A | 4/2006 |
| WO | 2006-033359 A1 | 3/2006 |

OTHER PUBLICATIONS

International Search Report of PCT/JP2007/074128, Mailing Date of Jan. 22, 2008.
Blakey et al, "Novel High-Index Resists for 193 nm Immersion Lithography and Beyond", Proc. of SPIE, 2007, p. 651909-1-9, vol. 6519, cited in spec.
J. Heijboer et al, "Study of the Molecular Movement of Oxa- and Thiacyclohexyl Rings in Solid Polymers by Mechanical Measurements over a Broad Frequency Range", Journal of Macromolecular Science—Physics, Jun. 1971, p. 375-392, cited in spec.

* cited by examiner

*Primary Examiner* — John Chu
(74) *Attorney, Agent, or Firm* — Westerman, Hattori, Daniels & Adrian, LLP

(57) ABSTRACT

To provide a thiopyran derivative, having a structure expressed by the following general formula 1:

General Formula 1

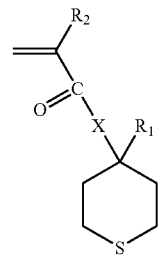

where X is O or S; $R_1$ is —H, —$CH_3$, C2-4 alkyl group, thioether group, or ketone group; $R_2$ is —H, —$CH_3$, or trifluoromethyl group; and $R_1$ and $R_2$ may be identical to or different from each other.

4 Claims, 3 Drawing Sheets

THIOPYRAN DERIVATIVE, POLYMER, RESIST COMPOSITION, AND METHOD FOR MANUFACTURING SEMICONDUCTOR DEVICE USING SUCH RESIST COMPOSITION

CROSS-REFERENCE TO RELATED APPLICATIONS

This application is a divisional application of Ser. No. 12/783,212, filed May 19, 2010, which is a continuation of PCT/JP2007/074128, filed on Dec. 14, 2007, the entire contents of which are incorporated herein by reference.

FIELD

The present invention relates to a novel thiopyran derivative, polymer containing the thiopyran as a monomer unit, a resist composition containing such the polymer, and a method for manufacturing a semiconductor device using such the resist composition.

BACKGROUND

In the current technology of the semiconductor integrated circuit, higher integration has been achieved and as a result, the minimum pattern size reaches the region of 100 nm or less. For the formation of fine patterns, exposure technique is regarded as very important, and the exposure technique enables to attain a desired pattern in the following manner. At first, a resist film is applied onto a substrate to be processed (surface to be processed) to which a thin film has been formed, the resist film is selectively exposed with light and then developed so as to form a pattern, a dry etching is performed using the thus obtained pattern as a mask, and finally the resist pattern is removed to obtain the desired pattern.

In order to realize downsizing of the pattern, it is effective to improve and develop both an exposure light source using the shorten wavelength and a resist material of high resolution corresponding to the characteristics of the exposure light source. Currently, ArF excimer laser exposure tools have been on the market. However, these exposure tools themselves are quite expensive and a large scale of cost is expected at the time the exposure tool is updated for the purpose of shortening the wavelength of the exposure tool. Moreover, it is not easy to develop a resist material which corresponds to the shorten wavelength of exposure light, and it is extremely difficult to realize the downsizing of the pattern by only shortening the wavelength of the exposure device.

For these reasons, much attention has been attracted to a new exposure technique, a liquid immersion lithography, in the art. In this method, the space between the projection lens and wafer in the exposure device is filled with liquid having a lager refractive index n than that of air so as to improve and obtain higher resolution than that of the related art.

The resolution of the exposure device is determined by using the following Calculation Formula 1:

Resolution $R$=Coefficient $k$×Wavelength $\lambda$ of light source/Numerical aperture NA      Calculation Formula 1

As represented with Calculation Formula 1, the resolution R improves (be smaller), as the wavelength $\lambda$ of an exposure light source is shorter and the numerical aperture NA is larger. Note that, the numerical aperture of the projection lens is represented as: NA=n×sin $\alpha$, where n is refractive index of a medium through which the exposure light is transmitted, and $\alpha$ is an angle formed between the exposure light and a light axis of the projection lens. Since the exposure of light is generally performed in atmospheric air, the refractive index n is 1 (i.e., n=1). The liquid immersion exposure method applies the exposure system in which the space between the projection lens and the wafer is filled with a liquid having the refractive index n larger than 1 (i.e., n>1). Accordingly, the refractive index is enlarged from 1 to n (a number larger than 1) in the relative formula of the numerical aperture NA: NA=n×sin $\alpha$. At the incident angle $\alpha$ of the same exposure light, the resolution R (minimum resolution size) will be reduced in 1/n as NA is enlarged n time(s). In addition, there is also the advantage such that, in the case where the value of NA is set the same, the depth of focus is deepened n times as $\alpha$ can be reduced by enlarging n.

In accordance with the conventional exposure in the air, the numerical aperture NA cannot be adjusted to 1 or larger, as a refractive index of the air between the resist and the lens becomes the factor to limit the numerical aperture NA. However, in accordance with liquid immersion lithography using water, the refractive index relative to the light having a wavelength of 193 nm is increased to 1.44. Therefore, it has been said that the numerical aperture NA can be increased up to about 1.4 on theory. However, as the numerical aperture NA is increased, the angle of the light incident to the resist film is significantly increased. Therefore, the depth of focus (a margin of the focal distance capable of resolution) is reduced. Moreover, to attain higher resolution (the smaller value of the resolution R), liquid immersion lithography of the next generation, which uses a medium having the higher refractive index (n>1.6) than that of water, has been studied. In the case of this liquid immersion lithography of the next generation, it is theoretically possible to increase the numerical aperture NA by about 1.6 times for the exposure in the air, but the current material for an ArF resist has the insufficient refractive index (the refractive index n is about 1.7 to the light having a wavelength of 193 nm). Therefore, the total reflection occurs on the surface of the resist film so that the light does not reach to the inner part of the resist film. As a result, an image cannot be formed, and hence a pattern cannot be formed.

To solve these problem, the studies have been conducted to increase a refractive index of a resist material. However, not so many materials, which can effectively increase a refractive index with maintaining transparency at 193 nm, without impairing acid reactivity desirable for forming a pattern, have not been known in the art. As a familiar example of the material whose refractive index is increased, a resin lens used for glasses and the like has been known. For such material, it is common that the refractive index of the material is increased by introducing heavy metals, aromatic rings, heavy halogen atoms such as bromine and iodine, or sulfur atoms into the material. In the case of the ArF resist material, however, there is a limitation in the method for introducing sulfur atoms because of the transparency at 193 nm, or the problem of contamination.

As prior examples of the resist material whose refractive index is increased, those using a resin containing sulfur, which has a problem in the transparency thereof, disclosed in Idriss Blakey et al., *Proc. SPIE*, 6519, 651909 (2007), an alicyclic material disclosed in Japanese Patent Application Laid-Open (JP-A) No. 2006-89412, and a curable composition containing aromatic heterocyclic (meth)acrylate disclosed in JP-A No. 2005-133071 have been known. Therefore, it has been desired to develop a material whose refractive index is increased, and which can be easily produced.

SUMMARY

The present invention aims at solving the problems present in the art, and achieving the following objects.

Accordingly, it is an object in one aspect of the invention to provide: a thiopyran derivative useful for increasing a refractive index of a resin for a resist composition without impairing transparency or acid sensitivity of the resist composition; a polymer containing the thiopyran derivative as a monomer unit; a resist composition containing the polymer; and a method for manufacturing a semiconductor device using the resist composition.

According to an aspect of the invention, a thiopyran derivative has a structure expressed by the following general formula 1:

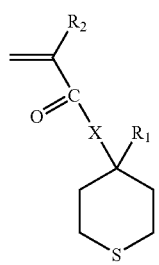

General Formula 1

In the general formula 1, X is O or S; $R_1$ is —H, —$CH_3$, C2-4 alkyl group, thioether group, or ketone group; $R_2$ is —H, —$CH_3$, or trifluoromethyl group; and $R_1$ and $R_2$ may be identical to or different from each other.

According to another aspect of the invention, a polymer contains a monomer unit containing the thiopyran derivative.

According to another aspect of the invention, the resist composition contains the polymer.

According to another aspect of the invention, the method for manufacturing a semiconductor device contains: forming a resist film formed of the resist composition on a processing surface; exposing the resist film to light; and developing the resist film so as to pattern the resist film.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Thiopyran Derivative

Figure 1:
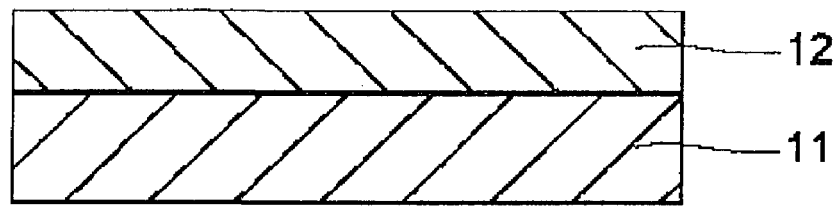
FIG. 1 is a schematic diagram explaining one example of a method for manufacturing a semiconductor device of the invention, and illustrates a state where an interlayer insulating film is formed on a silicon substrate.

The thiopyran derivative contains a structure expressed by the following general formula 1:

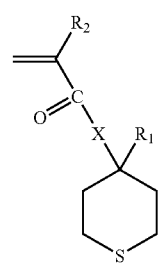

General Formula 1

In the general formula 1, X is O or S; $R_1$ is —H, —$CH_3$, C2-4 alkyl group, thioether group, or ketone group; $R_2$ is —H, —$CH_3$, or trifluoromethyl group; and $R_1$ and $R_2$ may be identical to or different from each other.

Since a sulfur element is contained in the thiopyran derivative, when a polymer containing this thiopyran derivative as a monomer unit (a constitutional unit) is used in a resist composition, a refractive index of the resin for the resist composition is increased without impairing the properties of the resist composition, such as transparency and acid sensitivity, and the resist composition can be applicable to the liquid immersion lithography of the next generation, which attempts to form a down-sized pattern using a lens of a large aperture (a lens having a large numerical aperture, NA).

The thiopyran derivative and the production method thereof will be explained hereinafter.

In General Formula 1, C3-4 alkyl group of $R_1$ may be of straight chain or branched chain, and preferable examples thereof include various propyl groups and butyl groups. Moreover, a thioester structure in which X is S is preferable for the purpose of increasing the refractive index, and such the structure is desirable.
Examples of the thiopyran derivative include the following compounds:
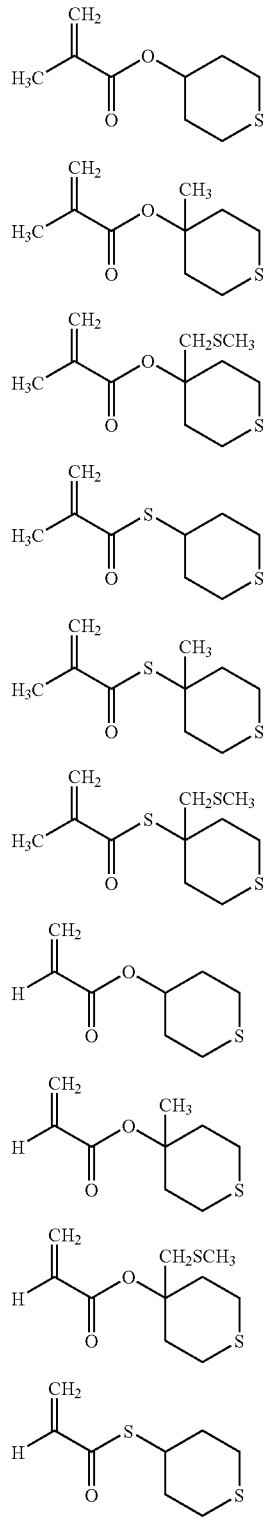
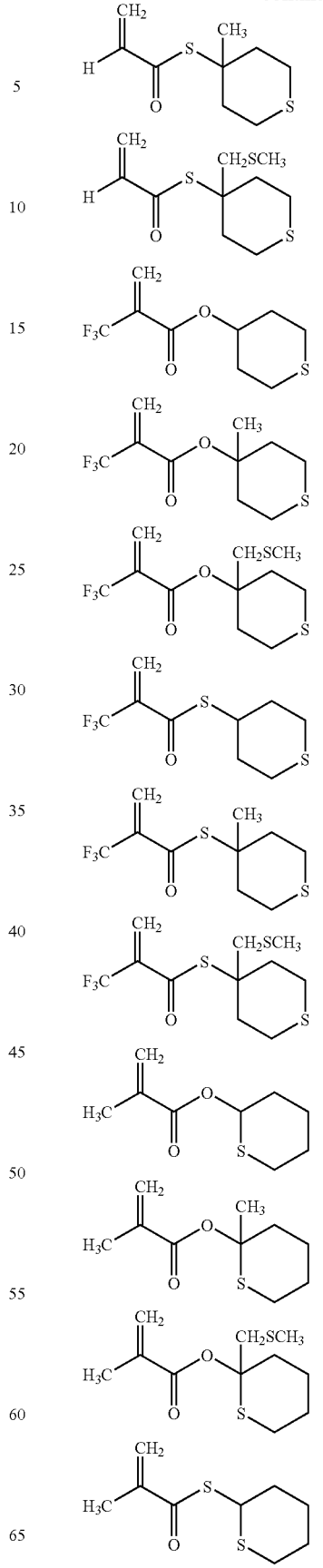

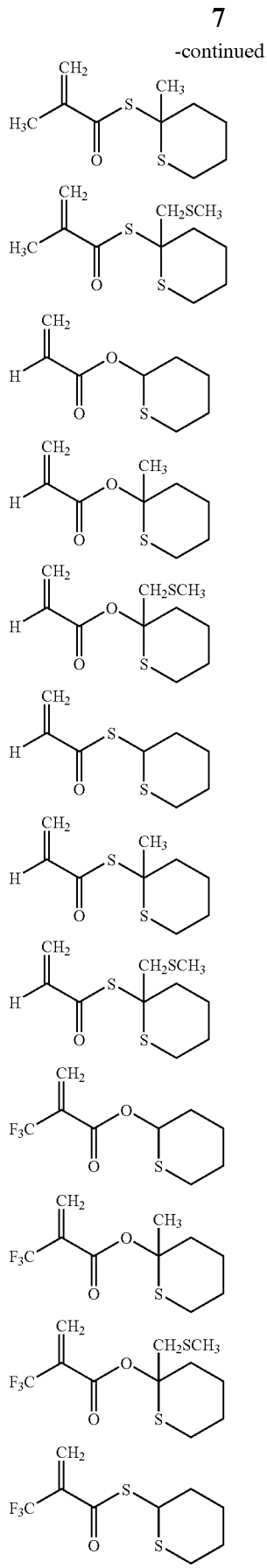

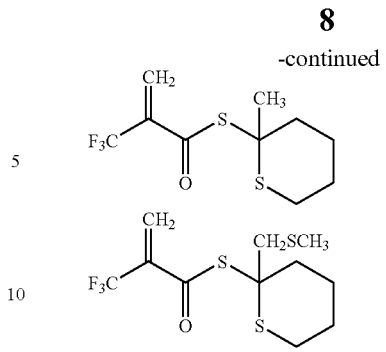

<Method for Manufacturing Thiopyran Derivative>

These thiopyran derivatives can be synthesized in accordance with the conventional methods, and as described in Idriss Blakey et al., *Proc. SPIE,* 6519, 651909 (2007), the thiopyran derivative can be generally obtained by an esterification reaction between acid chloride and an alcohol compound or a thiol compound. Specifically, for example, the same mole amounts of an alcohol or thiol compound and a base catalyst such as triethyl amine are added to a solvent such as dried methylene chloride, and the mixture is cooled down to 0° C. to −20° C. Thereafter, for example, acrylchloride was dropped thereto through a dropping funnel, triethyl amine salt is removed after loss of the raw material is conformed by a thin film chromatography or gas chromatography, and then purification is performed for example, by column chromatography to easily form a desired compound.

(Polymer)

Next, the polymer (the resin for a positive resist composition) containing the thiopyran derivative as a monomer unit will be explained.

The polymer is suitably selected depending on the intended purpose without any restriction, provided that it contains the thiopyran derivative as a monomer unit. For example, the thiopyran derivative may be copolymerized with other monomer units.

Since the polymer contains the monomer unit containing the thiopyran derivative, when a polymer containing this thiopyran derivative as a monomer unit is used in a resist composition, a refractive index of the resin for the resist composition is increased without impairing the properties of the resist composition, such as transparency and acid sensitivity, and the resist composition can be applicable to the liquid immersion lithography of the next generation, which attempts to form a down-sized pattern using a lens of a large aperture (a lens having a large numerical aperture, NA).

<Amount of Monomer Unit Containing Thiopyran Derivative in Polymer>

It is desirable that the amount of the monomer unit containing the thiopyran derivative in the polymer (the resin for a positive resist composition) be determined carefully considering the predetermined refractive index, resulting properties of a resist composition, such as sensitivity, resolution and etching resistance. The amount of the monomer unit containing the thiopyran derivative is preferably in the range of 0.1 mol % to 70 mol %, more preferably 10 mol % to 55 mol %. When the amount of the thiopyran derivative in the polymer is less than 10 mol %, the refractive index of the resulted resin for a resist composition cannot be increased. When the amount of the thiopyran derivative in the polymer is more than 55 mol %, an effect originated from other monomer units to be copolymerized (for example, high optical transparency and high etching resistance originated from adamanthyl group, or high adhesion originated from lactone group) cannot be attained, and absorption of ultraviolet rays is increased, reducing the transmittance of the light having a wavelength of 193 nm.

<Other Monomer Units>

The other monomer units can be suitably selected depending on the intended purpose without any restriction, but those monomer units having acid labile groups (e.g. monomer units having alicyclic groups that reacts with acid) are preferable. The resin for positive resist composition itself is generally alkali-insoluble, but the resin becomes alkali-soluble after the acid labile groups are reacted.

<<Acid Reactive Group>>

The acid reactive group is suitably selected depending on the intended purpose without any restriction. Preferably examples thereof include: tertially ester such as t-butyl group; acetal group such as ethoxyethyl, 3-oxocyclohexyl group, 2-alkyl-2-adamanthyl group, 1-alkyl-1-cyclopenthyl group, 1-alkyl-1-cyclohexyl group, 2-adamanthyloxymethyl group, 1-methyladamanthyloxymethyl group, and the like. Among them, the acid labile group having an alicyclic structure such as 2-alkyl-2-adamanthyl group, 2-adamanthyloxymethyl group, or 1-methyl adamanthyloxymethyl group is more preferable since such acid labile group provides etching resistance and transparency at the wavelength of 193 nm.

Moreover, the polymer preferably further contains a monomer unit including a lactone derivative (e.g., a monomer unit containing a lactone group that will be a side chain in a polymer). As a lactone ring is highly polar, the property contributes adhesion properties of a resist pattern, and it also imparts a suitable alkali-solubility at the exposed area due to its slight alkali-solubility.

<<Lactone Derivatives>>

A lactone derivative is suitably selected depending on the intended purpose without any restriction. Preferable examples thereof include γ-butyrolactone group, δ-lactone group, alicyclic lactone combined with norbornane or cyclohexane ring. The alicyclic lactone is particularly preferable since it contributes an etching resistance of the resulted resist composition.

In the case where the polymer (the resin) contains the monomer unit containing the thiopyran derivative, the monomer unit containing the acid labile group, and the monomer unit containing a lactone derivative, the ratio of these units is arbitral, but it is desirable that the ratio is adjusted considering the balance between resolution, etching resistance and refractive index.

Moreover, the polymer (the resin for positive resist) containing the monomer unit containing the thiopyran derivative may further contain monomer unit having other functions than mentioned above. Examples of such the unit include a unit containing an alkali-soluble group such as carboxyl group or hexafluorocarbinol group at a site which will be a side chain in the resulted polymer, a unit containing a hydroxyl group such as 2-hydroxyethyl group or 3-hydroxyadamanthyl group, and the like. The amount of these units in the polymer should be carefully determined for desired properties such as adhesion of the resist film to a substrate, alkali-dissolution rate of the exposed area, and the like.

(Resist Composition)

The resist composition is suitably selected depending on the intended purpose without any restriction, provided that it contains the aforementioned polymer. In the case of the positive resist composition, the resist composition contains an acid-generating agent together with the polymer (the resin).

A solvent used for the positive resist composition is suitably selected without any restriction, provided that it is commonly used for resist compositions, but is preferably selected considering solubility and coating performance of the polymer (the resin), the acid-generating agent, and other additives.

Moreover, the resist composition may further contain a quencher. By adding a quencher to the resist composition, the exposure contrast can be improved.

The resist composition may further contain a surfactant. A surfactant is added to the resist composition mainly for improving the coating performance thereof.

Moreover, the thiopyran derivative or homopolymer of the thiopyran derivative can be added to the positive resist composition as an additive, and such use of the thiopyran derivative or homopolymer is preferable. In the case where monomers of the thiopyran derivative are added as they are, it is desirable that the composition be prepared so that the monomers does not leach into a medium for liquid immersion. There is no problem in the addition of the monomers when the monomers will not leach. However, when the leaching of the monomers is concerned, it is preferred that, for example, a small amount (e.g., 0.5 parts by mass with respect to 100 parts by mass of the base resin) of a fluororesin or silicone resin, which easily causes a phase separation to an acrylic resin, be added to form a film which prevents the additive substances from leaching. The amount of the monomers can be appropriately adjusted depending on the desirable refractive index and patterning properties, but is preferably 50 parts by mass or less with respect to 100 parts by mass of the base resin.

In the case where homopolymer of the thiopyran derivative is added, any consideration is not particularly required as long as a resist film of a desirable quality can be formed, as the elution to the liquid immersion medium will not be a problem compared to the case of the monomer, but generally a phase separation tends to occur more easily. The amount of the homopolymer can be appropriately adjusted depending on the desirable refractive index and patterning properties, but is preferably 100 parts by mass or less with respect to 100 parts by mass of the base resin.

<Acid-Generating Agent>

The acid-generating agent is suitably selected from those known in the art without any restriction. Preferable examples thereof include commonly used trifluoromethanesulfonium salt, perfluorobutanesulfonium salt, perfluorodisulfoneimide salt, and the like. The amount thereof is preferably in the approximate range of 0.1 parts by mass to 10 parts by mass with respect to 100 parts by mass of the resin, though it will be adjusted depending on the balance with the sensitivity or resolution.

<Solvent>

The solvent is suitably selected depending on the intended purpose without any restriction. Preferable examples of such solvent include propylene glycol monomethylether acetate, 2-heptanone, ethyl lactate, and cyclohexanone. Optionally, an auxiliary solvent can also be used. As an auxiliary solvent, propylene glycol monomethyl ether or γ-butyrolactone is used preferably, and especially an organic solvent having a boiling point of about 100° C. to about 200° C. and excellent solubility of the resin is used preferably. A use of such the organic solvent is preferable, as it is suitably used for coating, and the rapid drying is prevented at the coating process.

<Quencher>

The quencher is suitably selected depending on the intended purpose without any restriction. Preferable examples thereof include nitrogen-containing compounds such as tri-n-octylamine, 2-methylimidazole, 1,8-diazabicyclo[5.4.0]undec-7-ene (DBU), 1,5-diazabicyclo[4.3.0]non-5-ene (DBN), diphenyl amine, triethanol amine, and the like.

<Surfactant>

The surfactant is suitably selected depending on the intended purpose without any restriction. Preferable examples thereof include nonionic surfactants free from metal ion such as sodium salt or potassium salt. Particularly preferable examples include polyoxyethylene-polyoxypropylene condensed derivatives, polyoxyalkylene alkyl ether, polyoxyethylene alkyl ether, polyoxyethylene derivative, sorbitane fatty acid ester, glycerin fatty acid ester, primary alcohol ethoxylate, phenol ethoxylate, silicone surfactant, and fluorosurfactant. Moreover, the surfactant may be selected from ionic surfactants other than the ones mentioned above, provided that the ionic surfactants are of metal salt-free. It is assumed that the same effect can be attained even if the aforementioned nonionic surfactant is replaced with such the metal salt-free ionic surfactant.

Since the resist composition contains the polymer, a refractive index of the resist base resin is increased without impairing the properties of the resist composition, such as transparency and acid sensitivity, and the resist composition can be applicable to the liquid immersion lithography of the next generation, which attempts to form a down-sized pattern using a lens of a large aperture (a lens having a large numerical aperture NA).

(Method for Manufacturing Semiconductor Device)

The method for manufacturing a semiconductor device at least contains a resist film forming step, an exposing step, and a developing step, preferably further contains a heating step, and may further contain suitably selected other steps, if necessary. It is preferred that the heating step be performed after the exposing step.

In the method for manufacturing a semiconductor device, a resist film formed of the resist composition is formed on a processing surface, followed by exposing the resist film to light. The resist film is then developed to form the patterned resist film.

<Resist Film Forming Step>

The resist film forming step is forming a resist film formed of the resist composition on a processing surface.

The resist film can be formed by a method known in the art, such as by coating. The coating method is suitably selected from the conventional coating methods depending on the intended purpose without any restriction. Preferable examples thereof include spin coating. In the case of the spin coating, as preferred conditions thereof, the rotation number is about 100 rpm to about 10,000 rpm, preferably 800 rpm to 5,000 rpm, and the duration is about 1 second to about 10 minutes, preferably 1 second to 90 seconds.

The thickness of the coating is suitably selected depending on the intended purpose without any restriction.

It is preferred that the coated resist composition be pre-baked (heated and dried) during or after coating. The conditions and method of the pre-baking are suitably selected depending on the intended purpose without any restriction, provided that the pre-backing will not soften the resist film. For example, the temperature of the pre-baking is preferably about 40° C. to about 150° C., more preferably 80° C. to 120° C., and the duration thereof is preferably about 10 seconds to about 5 minutes, more preferably 30 seconds to 90 seconds.

The processing surface is suitably selected depending on the intended purpose without any restriction. In the case where the resist film is formed in an electronic device such as a semiconductor, examples of the processing surface include surface layers of various members of the semiconductor device, preferably a substrate such as a silicon wafer and a surface thereof, and a low dielectric film such as various oxide films and a surface thereof.

The low dielectric film is suitably selected depending on the intended purpose without any restriction, and is preferably a film having a dielectric constant of 2.7 or less.

Preferable examples of such the low dielectric film include a porous silica film, and a fluororesin film.

The porous silica film can be formed, for example, by applying a material for forming a silica film, subjecting the applied material to a heat treatment so as to remove the solvent, and baking the applied material.

In the case where the fluororesin film is a fluorocarbon film, the fluororesin film can be formed, for example, by accumulating in accordance with a RFCVD method (power: 400 W) using a mixed gas of $C_4F_8$ and $C_2H_2$ or $C_4F_8$ gas as a source.

<Exposing Step>

The exposing step is selectively exposing the resist film to light.

The exposure can be suitably performed by means of the exposure device known in the art, and is carried out by applying light to the resist film. As a result of the application of the light, the photo acid-generating agent contained in the exposed area of the resist composition is decomposed to generate acid, causing a curing reaction of the resist composition to form a latent pattern.

The light is applied to a partial area of the resist film. The polarity of the resist film is increased as a result of that side chains of the resin are detached by the acid reaction in the partial area due to the application of the light, so that the highly polarized partial area is removed in the developing step described later to form a resist pattern.

In the exposing step, the application of light is carried out in accordance with liquid immersion lithography. Here, a medium for use in the liquid immersion lithography may be water, but is preferably liquid having a higher refractive index than that of water relative to light having a wavelength of 193 nm.

The exposure light is suitably selected depending on the intended purpose without any restriction. Preferably examples thereof include activation energy radiation such as ultraviolet ray, X-ray, electron ray, excimer laser beam, EUV light, and focused ion beam.

In the case where the ultraviolet ray is used, the ultraviolet ray having a wavelength of 200 nm or less is more preferable.

In the case where the excimer laser beam is used, KrF excimer laser light (wavelength of 248 nm), ArF excimer laser light (wavelength of 193 nm), $F_2$ excimer laser light (wavelength of 157 nm), or the like is preferable.

<Heating Step>

The heating step is subjecting the exposed resist film to a heating treatment (a post-exposure bake, PEB).

As a result of the heating, the elimination reaction of the side chain of the resist resin in the exposed area is accelerated.

The heating temperature is preferably 50° C. to 200° C., more preferably 70° C. to 180° C. When the temperature is less than 50° C., the elimination reaction of the side chain of the resin may not be progressed. When the temperature is more than 200° C., the resist composition, which forms the resist film, may be thermally decomposed.

<Development Step>

The development step is removing the exposed area of the resist film to develop the resist film, after exposing the resist film in the exposing step and reacting the exposed area of the resist film, so as to form a pattern of the resist film (a resist pattern).

The method for removing the reacted area is suitably selected depending on the intended purpose without any restriction, and examples thereof include a method for removing the reacted area using a developer.

The developer is suitably selected depending on the intended purpose without any restriction, and is preferably an alkali solution. Specific examples of the alkali solution include a tetramethylammoniumhydroxide (TMAH) solution, and a choline solution, which are commonly used in the production of a semiconductor device.

As a result of the developing, the area of the resist film where the light is applied is dissolved and removed to form (develop) a resist pattern.

<Other Steps>

Other steps are suitably selected depending on the intended purpose without any restriction. Examples thereof include a patterning step.

<<Patterning Step>>

The patterning step is etching the processing surface using the pattern of the resist film (the resist pattern) as a mask so as to pattern the processing surface.

The method for the etching is suitably selected from the methods known in the art depending on the intended purpose without any restriction. Preferable examples thereof include dry etching. The conditions of the etching are suitably selected depending on the intended purpose without any restriction.

The method for manufacturing a semiconductor device is suitable for the formation of various resist patterns, such as a line-space pattern, a hole pattern (for a contact hole), a pillar pattern, a trench pattern, and a line pattern, and the resist pattern formed by the method for manufacturing a semiconductor can be used, for example, as a mask pattern, and a reticle pattern, and are suitably used for the production of functional parts such as metal plugs, various wirings, magnetic heads, liquid crystal displays (LCD), plasma display panels (PDP), and a surface acoustic wave (SAW) filter, optical parts used for connection of optical wirings, minute parts such as microactuator, and a semiconductor device.

Specifically, by selectively depositing or etching using as a mask pattern, the resist pattern formed by the method for manufacturing a semiconductor device, a device having a fine processing pattern having a constant line width and formed of a metal or other materials can be manufactured, and for example, a semiconductor device having a fine wiring having a line width of 100 nm or less can be manufactured.

Moreover, in accordance with the method for manufacturing a semiconductor device, a fine and precise resist pattern can be accurately formed without causing the defects in the shape, and a higher performance semiconductor device having a fine wiring pattern, such as a flash memory, DRAM, and FRAM, can be efficiently mass-produced by using the resist pattern.

In accordance with the invention, there are provided a thiopyran derivative useful for increasing a refractive index of a resin for a resist composition without impairing properties of the resist composition such as transparency and acid sensitivity, a polymer containing a monomer unit containing the thiopyran derivative, a resist composition containing the polymer, and a method for manufacturing a semiconductor device using the resist composition.

Moreover, in accordance with the present invention, there can be provided: a thiopyran derivative, a polymer, and a resist composition, which are capable of forming a highly precise pattern by high refractive liquid immersion ArF excimer laser lithography that enables to draw the finer pattern, and thus largely contributes to the mass-production of devices; and a method for manufacturing a semiconductor device using the resist composition.

EXAMPLES

Examples of the invention will be explained hereinafter, but these examples shall not be construed as to limit the scope of the invention.

Synthesis Example 1

Synthesis of tetrahydro-2H-thiopyran-4-yl methacrylate (Thiopyran Derivative of the Following Formula 2)

To a 200-mL three-necked flask fitted with a stirrer bar coated with Teflon™, were added 5.37 g of 4-hydroxytetrahydrothiopyran (manufactured by SANKYO KASEI Co., Ltd.), 5.08 g of triethyl amine, and 50 mL of dried methylene chloride, and the mixture was stirred under nitrogen atmosphere at 0° C. To the mixture, 5.0 g of methacryloyl chloride was slowly added through a dropping funnel, and the resulted mixture was reacted at 0° C. for 40 minutes, allowed to warm to room temperature, and was further reacted for another 5 hours. After confirming loss of the starting material by a thin layer chromatography (TLC), the reaction solution was poured into a 300-mL separatory funnel, washed with 100 mL of water followed by 100 mL of saturated NaCl solution (brine), and dried with anhydrous sodium sulfate. From the obtained solution, the solvent was removed by an evaporator, to obtain an oily crude product. The crude product was purified by silica gel chromatography using a mixed solution of n-hexane and ethyl acetate to give 5.18 g of tetrahydro-2H-thiopyran-4-yl methacrylate (thiopyran derivative of the following formula 2) (yield: 61.3%).

(1) $^1$H-NMR (500 MHz, CDCl$_3$, internal standard TMS, in ppm): 1.95 (s, 3H), 1.9-2.1 (m, 4H), 2.58-2.81 (m, 4H), 4.93 (m, 1H), 5.57 (m, 1H), 6.12 (m, 1H)

(2) IR (KBr, cm$^{-1}$): 2920, 1716, 1635, 1292, 1163, 1018, 814

(3) Refractive index nD=1.506

Formula 2

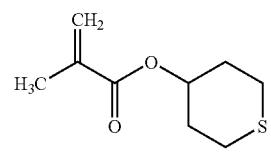

Synthesis Example 2

Synthesis of 4-methyl-tetrahydro-2H-thiopyran-4-yl methacrylate (Thiopyran Derivative of the Following Formula 3)

To a 200-mL three-necked flask fitted with a stirrer bar coated with Teflon™, were added 5.95 g of 4-hydroxy-4-methyltetrahydrothiopyran (manufactured by SANKYO KASEI Co., Ltd.), 5.08 g of triethyl amine, and 50 mL of dried methylene chloride, and the mixture was stirred under nitrogen atmosphere at 0° C. To the mixture, 5.0 g of methacryloyl chloride was slowly added through a dropping funnel, and the resulted mixture was reacted at 0° C. for 30 minutes, allowed to warm to room temperature, and was further reacted for another 5 hours. After confirming loss of the starting material by TLC, the reaction solution was poured in a 300-mL separatory funnel, washed with 100 mL of water followed by with 100 mL of saturated NaCl solution (brine), and dried with anhydrous sodium sulfate. From the obtained solution, the solvent was removed by an evaporator, to obtain an oily crude product. The crude product was purified by silica gel chromatography using a mixed solution of n-hexane and ethyl acetate to give 5.89 g of 4-methyl-tetrahydro-2H-thiopyran-4-yl methacrylate (thiopyran derivative of the following formula 3) (yield: 59.4%).

(1) $^1$H-NMR (500 MHz, CDCl$_3$, internal standard TMS, δ in ppm): 1.53 (s, 3H), 1.72 (m, 2H), 1.93 (d, 3H), 2.41-2.60 (m, 4H), 2.84-2.90 (m, 4H), 5.53 (q, 1H), 6.05 (d, 1H)

(2) IR (KBr, cm$^{-1}$): 2920, 1713, 1636, 1300, 1165, 1082, 920

(3) Refractive index nD=1.507

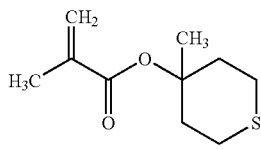

Formula 3

Synthesis Example 3

Synthesis of polytetrahydro-2H-thiopyran-4-yl methacrylate (Polymer of the Following Formula 4)

To a 100-mL eggplant-shaped flask fitted with a stirrer car coated with Teflon™, were added 1.39 g of tetrahydro-2H-thiopyran-4-yl methacrylate, and 5 mL of dioxane. The mixture was then stirred, and nitrogen gas was bubbled for 15 minutes to remove oxygen in the reaction atmosphere. To this, was added 0.37 g of AIBN as a radical polymerization initiator, and the flask was placed in an oil bath at 70° C. for 5 hours. The obtained reaction mixture was cooled to room temperature, and diluted with dioxane to be about 7 mL in volume. The solution was dropped into 250 mL of methanol with stirring to give white precipitate. After filtering with a glass filter, the obtained precipitated resin was dried in vacuo at 50° C. for 6 hours. The resulted resin was dissolved in about 7 mL of THF, was again precipitated in 250 mL of methanol, and filtered and dried in the aforementioned manner to provide polytetrahydro-2H-thiopyran-4-yl methacrylate (polymer of the following formula 4). The yield was 0.9 g, the weight average molecular weight was 12,800 (standard polystyrene equivalent), and polydispersion (Mw/Mn) was 1.88. Note that the molecular weight was measured by GPC(HLC-8220 GPC, manufactured by Tosoh Corporation).

(1) IR (KBr disk, cm$^{-1}$): 2947, 1724, 1429, 1269, 1149, 999, 871

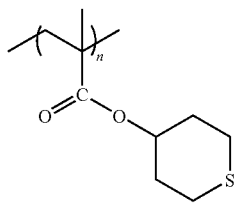

Formula 4

Synthesis Example 4

Synthesis of poly 4-methyl-tetrahydro-2H-thiopyran-4-yl methacrylate (Polymer of the Following Formula 5)

To a 100-mL eggplant-shaped flask fitted with a stirrer car coated with Teflon™, were added 1.3 g of 4-methyl-tetrahydro-2H-thiopyran-4-yl methacrylate, and 4 mL of dioxane. The mixture was then stirred, and nitrogen gas was bubbled for 15 minutes to remove oxygen in the reaction atmosphere. To this, was added 0.29 g of AIBN as a radical polymerization initiator, and the flask was placed in an oil bath at 70° C. for 4.5 hours. The obtained reaction mixture was cooled to room temperature, and diluted with dioxane to be about 10 mL in volume. The solution was dropped into 250 mL of methanol with stirring to give white precipitate. After filtering with a glass filter, the obtained precipitated resin was dried in vacuo at 50° C. for 6 hours. The resulted resin was dissolved in about 10 mL of THF, was again precipitated in 250 mL of methanol, and filtered and dried in the aforementioned manner to provide poly 4-methyl-tetrahydro-2H-thiopyran-4-yl methacrylate (polymer of the following formula 5). The yield was 0.75 g, the weight average molecular weight was 7,560 (standard polystyrene equivalent), and polydispersion (Mw/Mn) was 1.48. Note that the molecular weight was measured by GPC (HLC-8220 GPC, manufactured by Tosoh Corporation).

(1) IR (KBr disk, cm$^{-1}$): 2920, 1713, 1636, 1300, 1165, 1082, 920

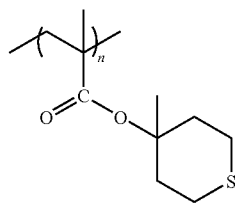

Formula 5

Synthesis Example 5

Synthesis of poly(2-methyl-2-adamanthyl methacrylate-tetrahydro-2H-thiopyran-4-yl methacrylate) (Polymer of the Following Formula 6)

To a 100-mL eggplant-shaped flask fitted with a stirrer car coated with Teflon™, were added 1.31 g of 2-methyl-adamanthyl methacrylate, 1.0 g of tetrahydro-2H-thiopyran-4-yl methacrylate, and 3.6 mL of dioxane. The mixture was then stirred, and nitrogen gas was bubbled for 15 minutes to remove oxygen in the reaction atmosphere. To this, was added 0.27 g of AIBN as a radical polymerization initiator, and the flask was placed in an oil bath at 70° C. for 5 hours. The obtained reaction mixture was cooled to room temperature, and diluted with dioxane to be about 20 mL in volume. The solution was dropped into 500 mL of methanol with stirring to give white precipitate. After filtering with a glass filter, the obtained precipitated resin was dried in vacuo at 50° C. for 6 hours. The resulted resin was dissolved in about 20 mL of THF, was again precipitated in 500 mL of methanol, and filtered and dried in the aforementioned manner to provide poly(2-methyl-2-adamanthyl methacrylate-tetrahydro-2H-thiopyran-4-yl methacrylate) (polymer of the following formula 6). The yield was 1.91 g, the weight average molecular weight was 18,300 (standard polystyrene equivalent), and polydispersion (Mw/Mn) was 2.19. Note that, the composition ration was determined by $^1$H-NMR (JNM-GX500, manufactured by JEOL Ltd.), and the molecular weight was measured by GPC(HLC-8220 GPC, manufactured by Tosoh Corporation).

(1) IR (KBr disk, cm$^{-1}$): 2912, 1722, 1257, 1155, 1103

Formula 6

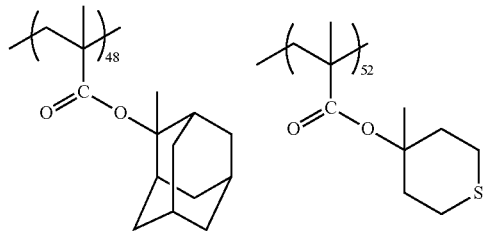

Synthesis Example 6

Synthesis of poly(2-methyl-2-adamanthyl methacrylate-γ-butyllacton-3-yl methacrylate-4-methyl-tetrahydro-2H-thiopyran-4-yl methacrylate) (Polymer of the Following Formula 7)

To a 100-mL eggplant-shaped flask fitted with a stirrer car coated with Teflon™, were added 1.31 g of 2-methyl-2-adamanthyl methacrylate, 0.57 g of γ-butyllacton-3-yl methacrylate, 0.62 g of 4-methyl-tetrahydro-2H-thiopyran-4-yl methacrylate, and 8.2 mL of dioxane. The mixture was then stirred, and nitrogen gas was bubbled for 15 minutes to remove oxygen in the reaction atmosphere. To this, was added 0.30 g of AIBN as a radical polymerization initiator, and the flask was placed in an oil bath at 70° C. for 5 hours. The obtained reaction mixture was cooled to room temperature, and diluted with dioxane to be about 20 mL in volume. The solution was dropped into 500 mL of methanol with stirring to give white precipitate. After filtering with a glass filter, the obtained precipitated resin was dried in vacuo at 50° C. for 6 hours. The resulted resin was dissolved in about 20 mL of THF, was again precipitated in 500 mL of methanol, and filtered and dried in the aforementioned manner to provide poly(2-methyl-2-adamanthyl methacrylate-γ-butyllacton-3-yl methacrylate-4-methyl-tetrahydro-2H-thiopyran-4-yl methacrylate) (polymer of the following formula 7). The yield was 1.7 g, the weight average molecular weight was 11,500 (standard polystyrene equivalent), and polydispersion (Mw/Mn) was 1.89. Note that, the composition ration was determined by $^1$H-NMR (JNM-GX500, manufactured by JEOL Ltd.), and the molecular weight was measured by GPC(HLC-8220 GPC, manufactured by Tosoh Corporation).

IR (KBr disk, cm$^{-1}$): 2910, 1790, 1720, 1257, 1178

Formula 7

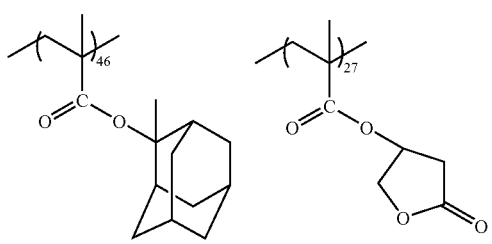

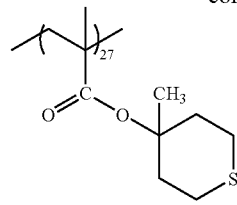

Examples 1 to 3, and Comparative Example 1

Measurement of Absorbance and Refractive Index

A resin solution was prepared using each of the resins of Synthesis Examples 3 to 5 each expressed by Formulae 4 to 6 and the commonly available resin for an ArF resist composition expressed by the following formula 8. Specifically, 900 parts by mass of propylene glycol monomethyl ether acetate (PGMEA) was added to 100 parts by mass of each resin to provide the resin solution. The obtained solution was filtered through a 0.2 μm Teflon™ membrane filter to remove particles. The resulted solution was spin-coated on a silicon wafer, and baked at 110° C. for 60 seconds to form a resin film. The refractive index of each resin film was measured by a spectral ellipsometer (GES-5, manufactured by SOPRALAB). In the same manner to the above, the absorbance of each resin was measured at 193 nm. The results are presented in Table 1.

Formula 8

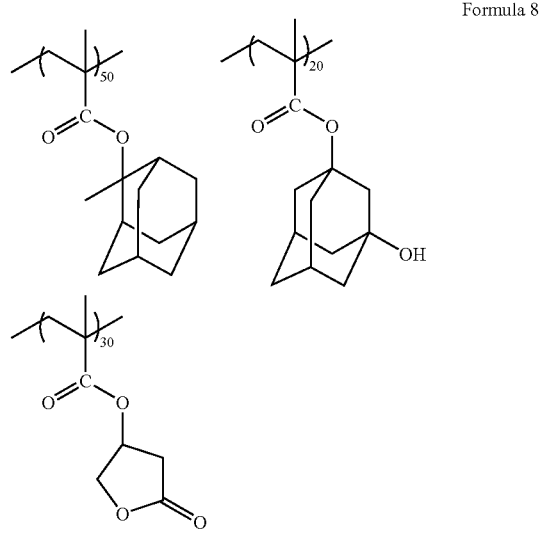

TABLE 1

| Resin solution | Refractive index (400-850 nm) | Absorbance (/μm) | Transmittance % (film thickness: 150 nm) |
|---|---|---|---|
| Ex. 1 | Formula 4 | 1.554 | 1.48 | 60.0 |
| Ex. 2 | Formula 5 | 1.524 | 1.79 | 53.9 |
| Ex. 3 | Formula 6 | 1.521 | 0.82 | 75.3 |
| Comp. Ex. 1 | Formula 8 | 1.504 | 0.20 | 93.2 |

In Table 1, the transmittance of light is shown with the value that is converted into that of the film having a thickness of 150 nm. As seen from Table 1, all the resins have transmittance of more than 40%, which is the lower limit for the pattern resolution, and thus these resins have transparency which is not problem in the practical use. Moreover, the refractive index is the refractive index to the light having a wavelength range of 400 nm to 850 nm. It has been known that the material having a high refractive index to light having a wavelength of 193 nm also has a high refractive index to light having the longer wavelength. As has been described above, when the resin having a side chain containing thiopyran is used, the refractive index is desirably increased while maintaining the transmittance low, compared to the conventional resin for the ArF resist composition (Comparative Example).

Examples 4 and 5

Preparation of Resist Composition

A resist composition for liquid immersion lithography was prepared in the accordance with the following formulation, using each of the polymers (resins) expressed by Formulae 6 and 7. As an acid-generating agent, triphenylsulfonium nonafluorobutane sulfonate (manufactured by Midori Kagaku Co., Ltd.) was used, and as a resist solvent, PGMEA was used.

| Resin | 100 parts by mass |
| Acid-generating agent | 3 parts by mass |
| Tri-n-octyl amine | 0.02 parts by mass |
| PGMEA | 900 parts by mass |

—Comparison in Resist Performance—

Onto a substrate to which an undercoat antireflection film (BARC, ARC-39, manufactured by Nissan Chemical Industries, Ltd.), the prepared resist composition was spin-coated, and baked at 110° C. for 60 seconds to form a resist film having a thickness of 250 nm. Each resist film was subjected to ArF liquid immersion lithography, and the sensitivity thereof was compared when the L/S pattern in the size of 200 nm was formed.

TABLE 2

| | Resist composition | Sensitivity (mJ/cm$^2$) | Residual |
|---|---|---|---|
| Ex. 4 | Formula 6 | 40 | None |
| Ex. 5 | Formula 7 | 35 | None |

As seen from above, the resist composition using the resin having a side chain containing thiopyran has sufficient sensitivity without residual in the exposed area.

Example 6

Production of Semiconductor Device

Figure 2:
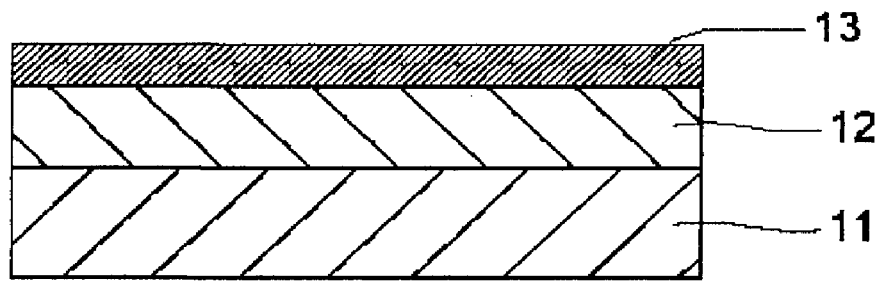
FIG. 2 is a schematic diagram explaining one example of a method for manufacturing a semiconductor device of the invention, and illustrates a state where a titanium film is formed on the interlayer insulating film of FIG. 1.
Figure 3:
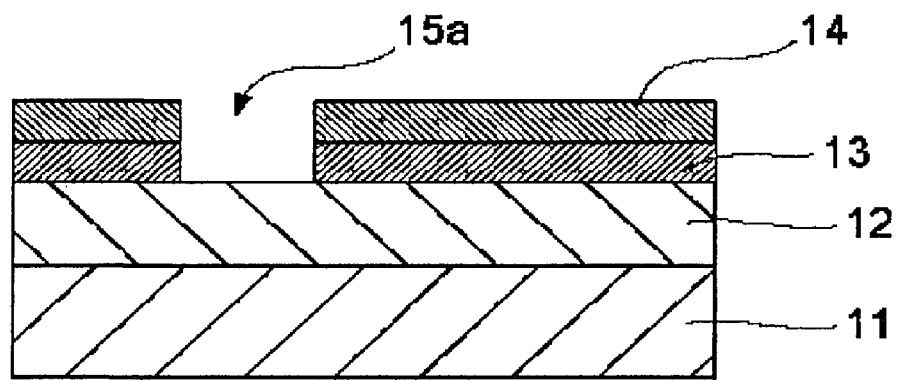
FIG. 3 is a schematic diagram explaining one example of a method for manufacturing a semiconductor device of the invention, and illustrates a state where a resist film is formed on the titanium film, and a hole pattern is formed in the titanium film.
Figure 4:
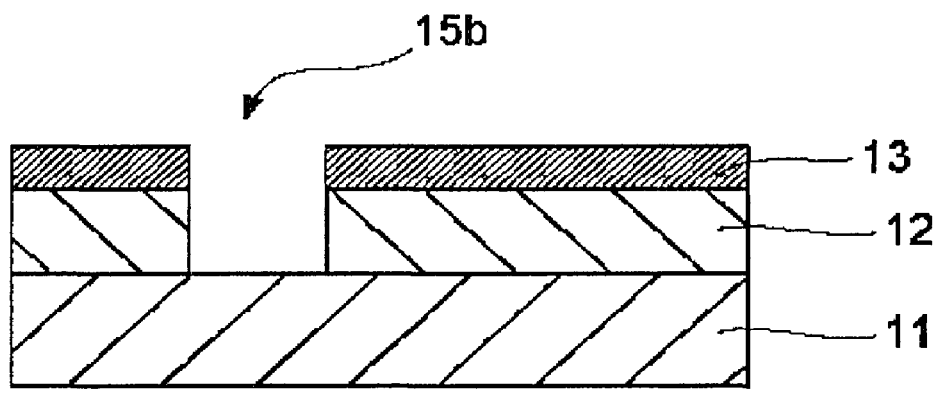
FIG. 4 is a schematic diagram explaining one example of a method for manufacturing a semiconductor device of the invention, and illustrates a state where the hole pattern is also formed in the interlayer insulating film.

An interlayer insulating film 12 was formed on a silicon substrate 11 as illustrated in FIG. 1, and a titanium film 13 was formed on the interlayer insulating film 12 in accordance with a sputtering method as illustrated in FIG. 2. Sequentially, a resist pattern 14 was formed by an ArF liquid immersion exposure as illustrated in FIG. 3, and using the resist pattern 14 as a mask, the titanium film 13 was subjected to patterning by reactive ion etching so as to form an opening 15a. The reactive ion etching was continuously preformed so as to remove the resist pattern 14, as well as forming an opening 15b in the interlayer insulating film 12 using the titanium film 13 as a mask as illustrated in FIG. 4.

Figure 5:
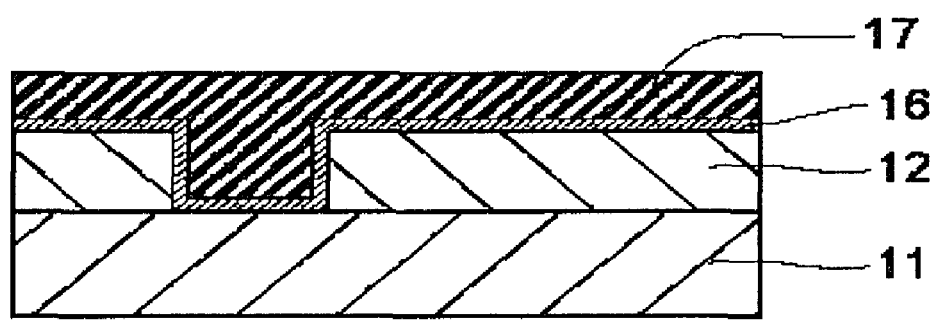
FIG. 5 is a schematic diagram explaining one example of a method for manufacturing a semiconductor device of the invention, and illustrates a state where a Cu film is formed on the interlayer insulating film to which the hole pattern has been formed.
Figure 6:
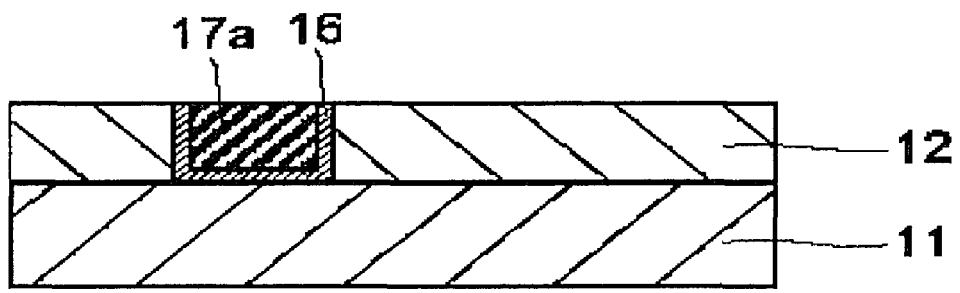
FIG. 6 is a schematic diagram explaining one example of a method for manufacturing a semiconductor device of the invention, and illustrates a state where the Cu deposited on the interlayer insulating film other than on the hole pattern is removed.

Thereafter, the titanium film 13 was removed by a wet treatment, and a TiN film 16 was formed on the interlayer insulating film 12 in accordance with a sputtering method as illustrated in FIG. 5 and a Cu film 17 was sequentially formed on the TiN film 16 in accordance with an electroplating method. As illustrated in FIG. 6, the surface was smoothened by CMP while leaving only a barrier metal and the Cu film (first metal film) in a trench corresponding to the opening 15b (FIG. 4) so as to form a wiring 17a of a first layer.

Figure 7:
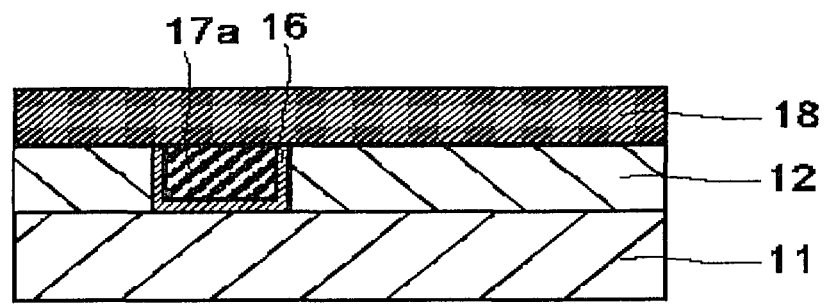
FIG. 7 is a schematic diagram explaining one example of a method for manufacturing a semiconductor device of the invention, and illustrates a state where an interlayer insulating film is formed on the Cu plug formed in the hole pattern and on the TiN film.
Figure 8:
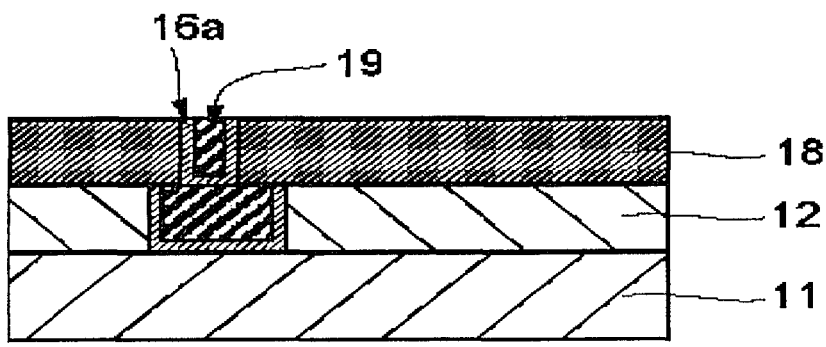
FIG. 8 is a schematic diagram explaining one example of a method for manufacturing a semiconductor device of the invention, and illustrates a state where a hole pattern is formed in the interlayer insulating layer as the surface layer, and a Cu plug is formed therein.

Thereafter, an interlayer insulating film 18 was formed on the wiring 17a of the first layer as illustrated in FIG. 7, and then, as illustrated in FIG. 8, onto the wiring 17a of the first layer, a Cu plug (second metal film) 19 and a TiN film 16a which would be connected with a wiring of an upper layer formed later were formed in the same manner as illustrated in FIGS. 1 to 6.

Figure 9:
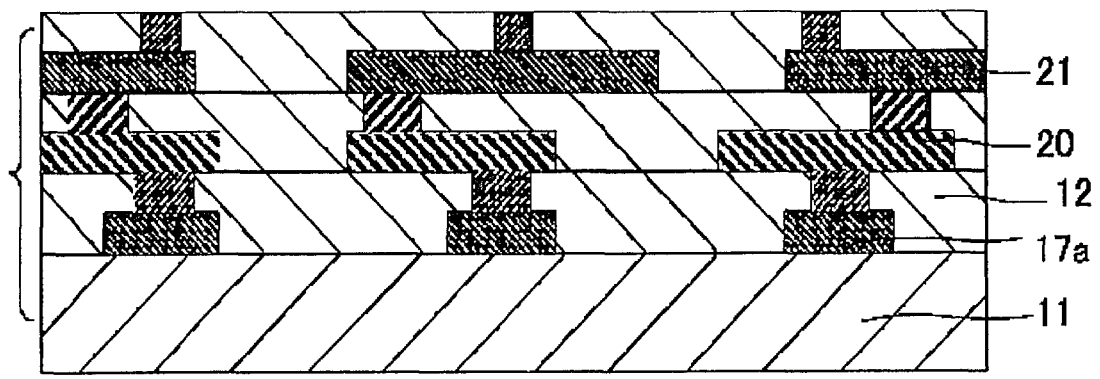
FIG. 9 is a schematic diagram explaining one example of a method for manufacturing a semiconductor device of the invention, and illustrates a state where a three-layered wiring is formed.

By repeating each aforementioned process, a semiconductor device having a multi-layered wiring structure containing the first layer wiring 17a, the second layer wiring 20 and the third layer wiring 21 disposed on the silicon substrate 11 was formed as illustrated in FIG. 9. Note that, barrier metal layers each formed under each wiring were not illustrated in FIG. 9.

In Example 6, the resist pattern 14 was a resist pattern formed by using the resist composition of the invention. Moreover, the interlayer insulating film 12 was formed with a low dielectric constant material having a dielectric constant of 2.7 or less, e.g. a porous silica film (CERAMATE NCS, manufactured by JGC Catalysts and Chemicals Ltd., dielectric constant: 2.25), or a fluorocarbon film (dielectric constant: 2.4) accumulated in accordance with a RFCVD method (power: 400 W) using a mixed gas of $C_4F_8$ and $C_2H_2$ or $C_4F_8$ gas as a source.

In the examples above, the production methods of the thiopyran derivative, or the polymer containing the monomer unit containing the thiopyran derivative. However, these production methods are described as examples, and it should be noted that the thiopyran derivative or the polymer can be also obtained in other conventional methods.

Moreover, the method for manufacturing a semiconductor can be applied to the productions of those having a fine pattern, e.g., a mask pattern, a reticle pattern, functional parts such as metal plugs, various wirings, magnetic heads, liquid crystal displays (LCD), plasma display panels (PDP), and a surface acoustic wave (SAW) filter, optical parts used for connection of optical wirings, and minute parts such as microactuator. In such productions, the same effects can be attained due to the same functions.

Moreover, in the example above, the production process of the flash memory was specifically explained as an example of the semiconductor, but the example thereof shall not be restricted to the flash memory. The method for manufacturing a semiconductor can also provide the same effect when it is applied to the production process of a logistic device, that of DRAM, or that of FRAM.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification related to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A method for manufacturing a semiconductor device, comprising:
   forming a resist film formed of a resist composition on a processing surface;
   selectively exposing the resist film to light; and
   developing the resist film so as to pattern the resist film,
   wherein the resist composition contains a monomer unit containing a thiopyran derivative having the structure expressed by the general formula 1:

General Formula 1

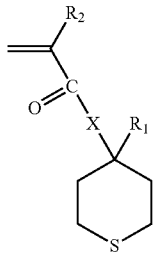

to where X is O or S; $R_1$ is —H, —$CH_3$, C2-4 alkyl group, thioether group, or ketone group; $R_2$ is —H, —$CH_3$, or trifluoromethyl group; and $R_1$ and $R_2$ may be identical to or different from each other.

2. The method according to claim 1, wherein the selectively exposing is selectively exposing the resist film to light in accordance with liquid immersion lithography, and a medium used for the liquid immersion lithography is either water or a liquid having higher refractive index than that of water with respect to light having a wavelength of 193 nm.

3. The method according to claim 1, further comprising etching the processing surface using the pattern of the resist film as a mask so as to pattern the processing surface.

4. The method according to claim 3, wherein the processing surface is a surface of a base, the base being formed of an insulating material having a dielectric constant of 2.7 or less.

* * * * *